United States Patent [19]
Alarcon-Lopez et al.

[11] Patent Number: 5,667,549
[45] Date of Patent: Sep. 16, 1997

[54] METHOD AND SYSTEM TO AUTOMATICALLY LIFT THE CURTAINS OF THE EXIT HOOD OF A MACHINE FOR THE PRODUCTION OF FLOAT FLAT GLASS

[75] Inventors: Manuel Alarcon-Lopez, Bondojito; Lenin Roman-Gomez, Ecatepéc; Rafael-Jorge Rojas-Cortes, Tlalnepantla; Victor-Octavio Enciso-Aguilar, Morelos, all of Mexico

[73] Assignee: Vidrio Plano de Mexico, S.A. de C.V., San Juan Ixhuatepec, Mexico

[21] Appl. No.: 591,770

[22] Filed: Jan. 25, 1996

[51] Int. Cl.$^6$ .................................................. C03B 18/02
[52] U.S. Cl. .................... 65/29.18; 65/99.1; 65/158; 65/160; 364/473.01
[58] Field of Search ........................ 65/29.12, 158, 65/99.1, 99.2, 160, 165, 182.1, 29.18; 364/473.01, 468.16, 468.17

[56] References Cited

U.S. PATENT DOCUMENTS

| 2,621,808 | 12/1952 | Blakeney | 65/160 |
|---|---|---|---|
| 2,625,658 | 1/1953 | Robinson | 65/160 |
| 3,251,667 | 5/1966 | Touvay | 65/99.1 |
| 4,585,343 | 4/1986 | Schave et al. | 65/29.12 |
| 4,665,392 | 5/1987 | Koontz . | |

FOREIGN PATENT DOCUMENTS

| 50-22048 | 7/1975 | Japan | 65/160 |
|---|---|---|---|
| 60-107547 | 6/1985 | Japan | 65/158 |

OTHER PUBLICATIONS

COMAX Laser Level Gauge Product Data LL 01 Information Sheet, Courser Inc., Elmira, New York, 6 pages Dec. 1980.

*Primary Examiner*—Steven P. Griffin
*Attorney, Agent, or Firm*—Abelman, Frayne & Schwab

[57] ABSTRACT

A system and method is disclosed to automatically lift the curtains of the exit hood of a machine for the production of float flat glass by the floating process. A light beam emitter is provided for a light beam which strikes the surface of the glass ribbon, being formed, and is reflected by that surface. A light beam receptor receives the light beam reflected by the surface of the glass ribbon and provides a signal representative of the absence or deviation of the reflected light beam should there be a break in the glass ribbon. A controller receives the signal representative of the absence or deviation of the reflected light beam, and provides operating signals to the actuators of the i) curtain lifting mechanism, ii) reheating system, iii) glass edge follower mechanism and iv) alarm of the glass ribbon forming machine. These signals automatically a) lift the curtains to avoid clogging of the broken glass ribbon, b) operate the reheating system of the exit hood, c) retract the glass edge follower mechanism, and d) trigger the to allow for a rapid restoration of the glass ribbon forming process.

5 Claims, 3 Drawing Sheets

METHOD AND SYSTEM TO AUTOMATICALLY LIFT THE CURTAINS OF THE EXIT HOOD OF A MACHINE FOR THE PRODUCTION OF FLOAT FLAT GLASS

BACKGROUND OF THE INVENTION

1. Field of the Invention

This invention is related to a machine and its method of operation for the production of float flat glass by the floating process, and more specifically to a system to automatically lift the outlet curtains of the exit hood of the machine, operate the reheating system of the floating chamber, retract the glass edge follower mechanism of the glass ribbon, and trigger the alarm of the glass forming machine, so as to allow for the rapid restoration of the glass ribbon forming process.

2. Description of the Related Art

At the outlet of the floating chamber of the typical machine for producing float flat glass by the floating process, there is a series of curtains within the equipment. This part of the equipment, known as the "exit hood", act as gates to avoid heat loss from the exit hood and floating chamber.

The height of these curtains is commonly adjusted by a manually operated mechanical positioning system. The curtains can be lifted to their maximum height in the case of an emergency, usually by a pneumatic motor, coupled to the positioning system.

In the case of a control failure in the glass ribbon forming process, which normally results in a breakage of the glass ribbon, it is necessary that an operator at the forming zone, trigger the alarm of the machine and rapidly lift the curtains to their maximum height using the pneumatic system. This is necessary to avoid the broken glass ribbon from clogging the curtains. Thus, it is absolutely necessary to have an operator continuously inspecting this zone of the forming process.

Other components of the machine, such as the reheating system of the glass chamber which compensates for thermal looses at the curtains, and the glass edge follower mechanism which helps in guiding the glass ribbon and which has to be withdrawn in case of a breakage to avoid the broken glass from clogging at the curtains, among others, also have to be controlled in case of a breakage of the glass ribbon. The controls should also allow a rapid restoration and continuation of the forming process without inconvenient loss of time, energy and materials.

If the operator takes such emergency actions in a minimum of time, the process can be rapidly restored. Otherwise, the broken glass ribbon will obstruct the outlet at the curtains and will cause an interruption of the forming process with the consequent loss of material and thermal equilibrium.

According to the present invention, the curtains are automatically lifted immediately upon breakage of the glass ribbon, and other actions are taken to avoid undesirable interruptions of the process. This system has been developed after research to find a solution that does not depend on the operator's awareness of the problem and response time. Hence, applicants have invented a system which automatically and immediately takes such actions upon detecting such glass breaking.

The detection of a breaking of the glass ribbon, is carried out, in accordance with the present invention, by the incidence of a light beam on the glass surface. The reflected light beam, provides a signal representative of the absence or deviation of the light beam because of a breakage of the glass ribbon. This signal is fed to a data processor which, upon receiving the signal representative of the absence of the light beam, provides operating signals to actuators to operate i) the curtain lifting mechanism, ii) the reheating system of the glass chamber (to keep a thermal equilibrium), iii) the glass edge follower mechanism (to retract it and avoid clogging), and iv) to trigger the alarm of the machine, to carry out other necessary control operations to allow for a rapid restoration of the process.

Some advantages of the system of the present invention as described above, are that the system will automatically and immediately carry out the necessary steps to avoid clogging of the broken glass ribbon at the curtains and other components at the floating chamber, without depending on the human operator's recognition of the problem and of the time for the operator's response to an urgent solution.

Consequently, other advantages of the present invention are that the system will save energy and material by restoring the normal process conditions in a minimum time, to continue the glass ribbon forming process.

An apparatus is presently known for detecting the presence of a mark (usually a trademark) on a transparent substrate. This apparatus, as disclosed in Koontz, U.S. Pat. No. 4,665,392, includes a light beam emitter to provide a light beam through the upper surface of the transparent substrate. The light beam is received by a detector on the opposite face of the substrate to provide a signal representative of the mark on the substrate to take the necessary steps in an application station for printing such marks. However, this apparatus is absolutely different from the system herein disclosed. This is for an entirely different purpose and operated under different concepts as the system of the present invention.

SUMMARY OF THE INVENTION

It is therefore a main object to the present invention to provide a system to automatically lift the curtains of the exit hood of a machine for the production of float flat glass by the floating process. In case of a break of the glass ribbon, the broken glass is prevented from clogging at the output of the floating chamber.

It is also a main object of the present invention, to provide a system to automatically lift the curtains of the exit hood of a machine for the production of float flat glass by the floating process, of the nature above disclosed, by providing an emitter for the incidence of a light beam on the surface of a glass ribbon. The light beam is then reflected by the glass and received by a receptor at the other edge of the glass ribbon, to provide signals to a data processor, which in turn provides control signals to immediately lift the curtains in the absence or deviation of the reflected light beam at the receptor and allow a fast restoration of the production process.

It is an additional main object of the invention, to provide a system to automatically lift the curtains of the exit hood of a machine for the production of float flat glass by a floating process, of the nature above disclosed, which will i) automatically lift the curtains to avoid clogging of the broken glass ribbon at the curtains, ii) stop of the process, iii) operate the reheating system of the floating chamber to keep a thermal equilibrium therein, and iv) retract the glass edge follower mechanism from the glass ribbon to avoid clogging therein, all of this to allow restoration of the process in a minimum of time.

It is still a main object of the invention, to provide a system to automatically lift the curtains of the exit hood of a machine for the production of float flat glass by the floating process, of the nature above disclosed, which will trigger an alarm at the forming machine and carry out all the necessary control operations to allow continuation of the process.

It is a further main object of the invention, to provide a method to automatically lift the curtains of the exit hood of a machine for the production of float flat glass by a floating process, by: 1) the incidence of a light beam on the surface of a glass ribbon, to be reflected thereby, 2) receiving the reflected light beam to derive a signal representative of the absence or deviation of the beam, 3) deriving control signals from said signal representative of the absence or deviation of the light beam, and 4) providing said control signals to actuators of the curtain lifting mechanism, to automatically and immediately lift the curtains.

These and other objects and advantages of the system of the present invention will be apparent from the following detailed description of the embodiment of the invention, provided in combination with the accompanying drawings.

DETAILED DESCRIPTION OF THE EMBODIMENTS OF THE INVENTION

Figure 1:
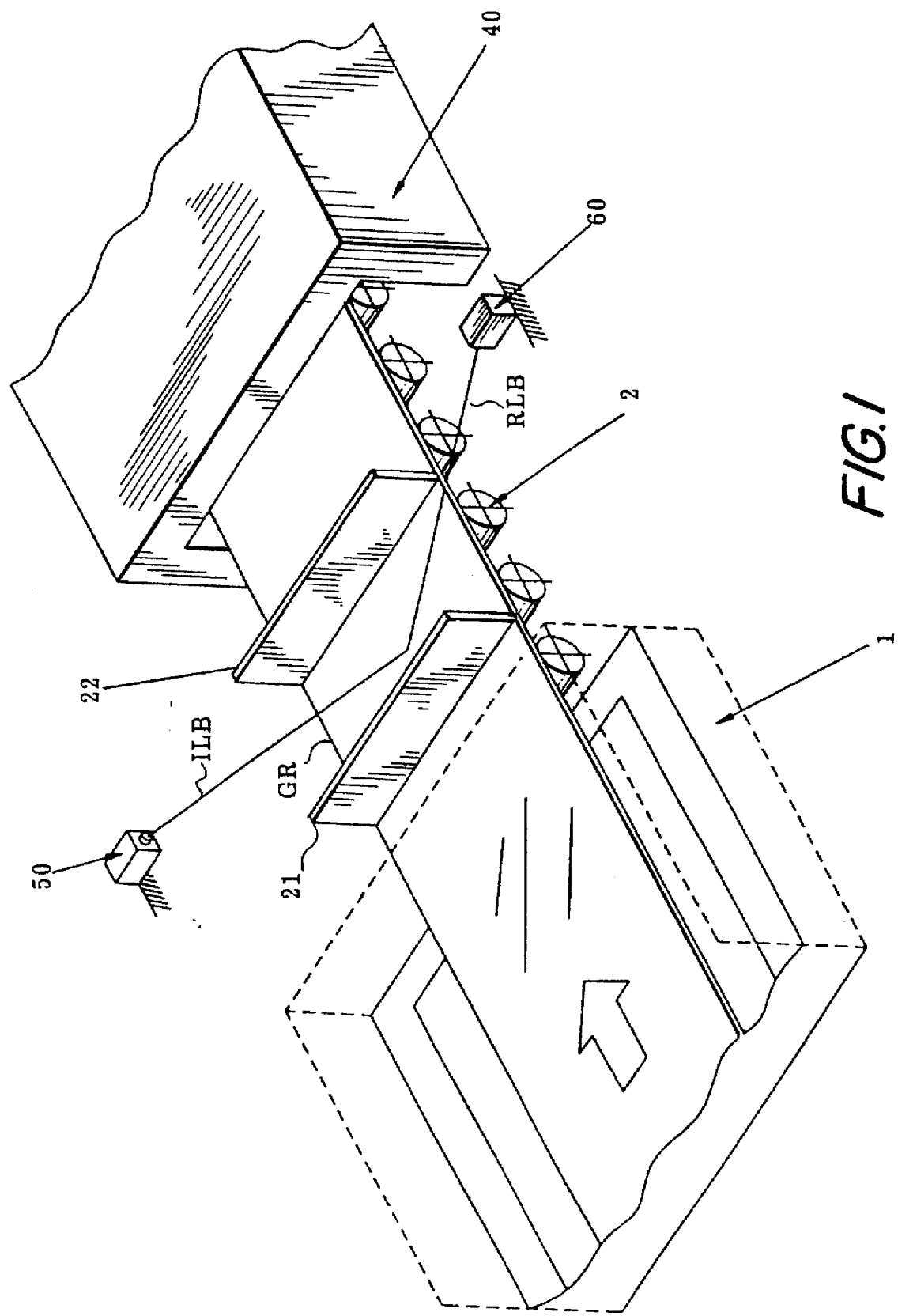
FIG. 1 is an schematic perspective view of a conventional floating machine for the production of float flat glass by a floating process, incorporating the system of the present invention to automatically lift the outlet curtains of the exit hood.
Figure 2:
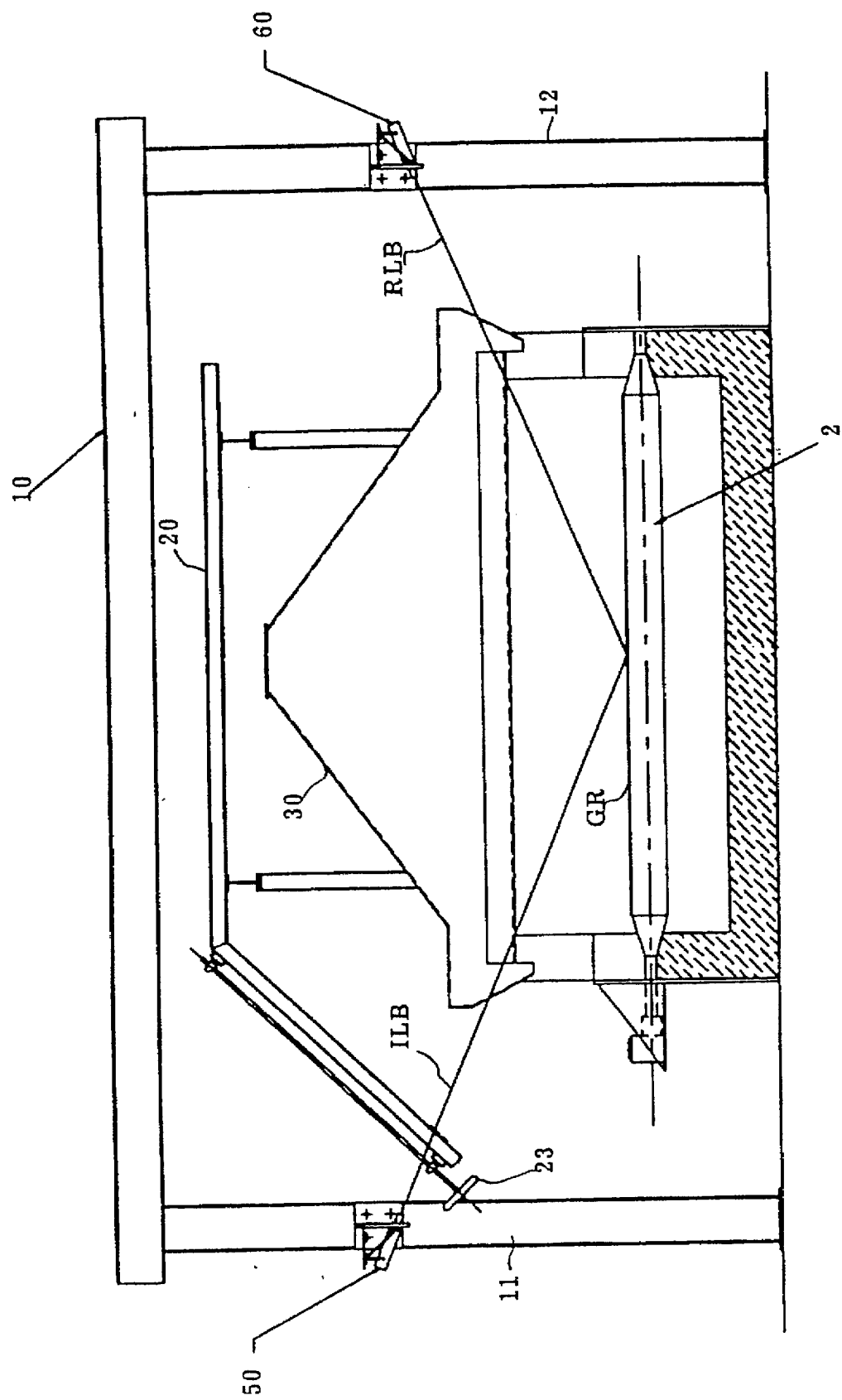
FIG. 2 is a front, partial cross section of the system of the present invention, to automatically lift the outlet curtains of the exit hood, in a machine for the production of float flat glass by a floating process.

Referring initially to FIGS. 1 and 2 of the drawings, there is shown a machine for the production of float flat glass by a floating process according to the present invention. It comprises a floating chamber 1, from which a glass ribbon is continuously emerging; a plurality of conveyor rollers 2 to convey the glass ribbon exiting from the floating chamber 1; and an exit hood structure 10 at the output of the floating chamber 1. The exit hood structure comprises side supports 11 and 12; and a holding structure 20 to hold a plurality of curtains 21 and 22. The curtains act as gates to avoid heat looses from the floating chamber 1. They can be lifted and lowered by means of a wheel mechanism 23 operated by hand to adjust the height of the curtains 21 and 22, and by means of an emergency mechanism (not illustrated) normally actuated by an operator to immediately lift the curtains 21 and 22 in case the operator observes that the glass ribbon GR is broken. The exit hood structure also includes a gas extractor 30 to extract the gases which could be accumulated in the exit hood structure 10. Finally, the glass ribbon is thermally treated at a tempering chamber 40 which properly is not a part of the forming machine.

Figure 3:
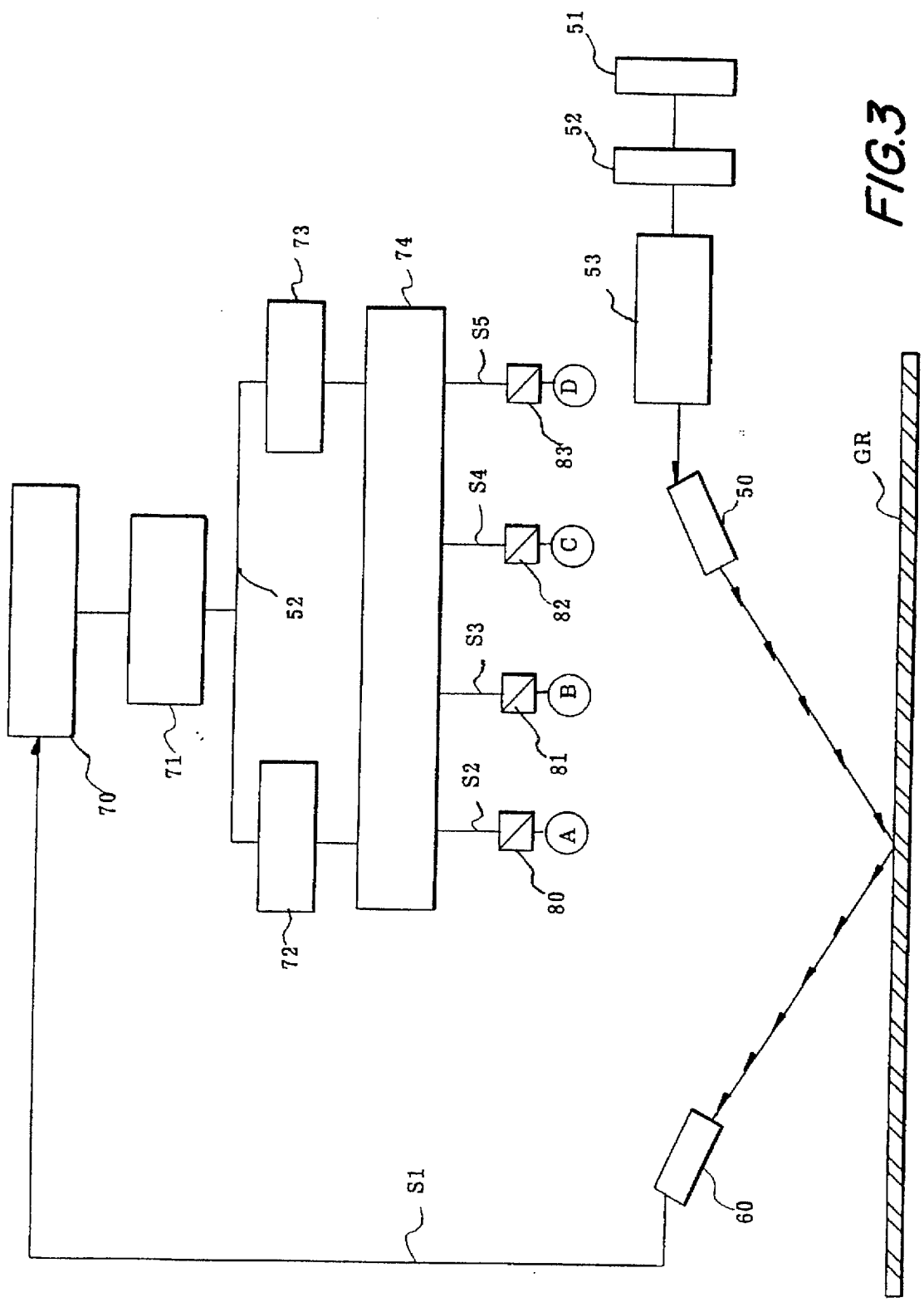
FIG. 3 is a block diagram of the system of FIGS. 1 and 2.

Reference is now also made to FIG. 3, which shows the system to automatically lift the curtains 21 and 22 of the exit hood 10 of a machine for the production of float flat glass by the floating process according to the present invention. The automatic system includes a light beam emitter 50 operated by a source of DC 51 through an on/off switch 52, which is operating a power source 53. The emitter 50 is held by a side support 11 of the exit hood structure 10, at an edge over the glass ribbon GR to provide a light beam ILB which is incident on a surface of the glass ribbon GR conveyed by the conveying rollers 2 and is reflected as a reflected light beam RLB by the glass surface of the glass ribbon GR. A light beam receptor 60 held by the other support 12 of the exit hood structure 10 at the outer edge over the glass ribbon GR, at a side opposed to the emitter 50, receives the reflected light beam RLB. Receptor 60 provides a signal S1 representative of the absence or deviation of the reflected light beam RLB because of break of the glass ribbon GR. A controller 70, which normally is an amplifier module AM, receives the signal S1 from beam receptor 60 and is representative of the absence or deviation of the reflected light beam RLM. Controller 70 processes this signal through a regulating source 71, to which are connected, timers 72 and 73 and an output relay 74. Output relay 74 provides operating signals S2, S3, S4 and S5 to on/off switches 80, 81 82 and 83 to respectively: trigger the emergency alarm A; operate the lifting mechanisms B of the curtains 21 and 22, to automatically lift them and avoid clogging of the broken glass ribbon GR at the curtains 21 and 22; operate the reheating system C, to compensate for and/or maintain the proper thermal conditions in the exit hood structure 10; and retract the glass edge follower mechanism D to prevent that mechanism from pushing the broken glass and create a clog at the curtains 21 and 22.

By taking all of the above actions the process operation conditions can be rapidly restored with a minimum time, saving time, glass and energy.

In a preferred embodiment of the system of the present invention, the light emitter 50 is a laser beam emitter, with the laser incident on or about a central portion of the glass ribbon at an angle of about 25°.

Accordingly, the method of the present invention to automatically lift the curtains of the exit hood of a machine for the production of float flat glass by a floating process comprises:

a) providing a light beam from a light emitter placed over an edge of the glass ribbon, as an incident beam on a surface of a glass ribbon, to be reflected thereby as a reflected light beam;

b) receiving the reflected light beam by a light beam receiver;

c) deriving a signal from the receiver, representative of the absence of the reflected light beam because of a break of the glass ribbon.

d) feeding to a controller, the signal representative of an absence of the light beam reflected by the glass ribbon, e) deriving operating signals from the controller; and f) providing the controller operating signals to the actuators of curtain lifting mechanisms: i) to automatically lift the curtains and avoid clogging of the broken glass at the curtains, ii) to a reheating system of the floating chamber to keep a thermal equilibrium therein, iii) to a glass edge follower mechanism to retract it from the glass ribbon to avoid the broken glass from being clogged therein, iv) to an emergency alarm of the machine to trigger it, and v) to carry out any other steps to restore the process at the normal stated conditions.

It is finally to be understood that the invention is not limited just to the above disclosed embodiment and that persons skilled in the art will be enabled by the teachings of this invention, to make changes in the design and disposition of the components of the present invention, which will be within the true spirit and scope of the invention as claimed in the following claims.

What is claimed is:

1. In a glass manufacturing machine for the production of float flat glass as a glass ribbon, which includes an exit hood for the glass ribbon, liftable curtains for the exit hood, and, a system to automatically lift the curtains of the exit hood, comprising:

light beam emission means placed over an edge of the glass ribbon, to provide a light beam incident on a surface of the glass ribbon to be reflected thereby as a reflected light beam;

light beam reception means placed over another edge of the glass ribbon, opposed to the emission means, to receive the reflected light beam and provide a signal representative of the absence or deviation of the reflected light beam because of a break in the glass ribbon;

control means for receiving the signal representative of the absence or deviation of the reflected light beam, and provide operating control signals including a first signal for actuating the system to automically lift the curtains of the exit hood in response to the absence or deviation of the reflected light beam.

2. The system of claim 1, which further includes a glass edge follower mechanism and, wherein the operating control signals also include a second signal to trigger an emergency alarm;

a third signal to operate a reheating system at the exit hood, to compensate and/or maintain proper thermal conditions therein; and a fourth signal to retract the glass edge follower mechanism to prevent that mechanism from pushing broken glass to form a clog at the curtains.

3. The system of claim 1, wherein the light beam emission means is a laser beam emission means for generating a laser beam which is incident at an angle of about 25° on about a central portion of the glass ribbon.

4. In a float glass manufacturing machine for the production of float flat glass as a glass ribbon, which includes an exit hood for the float flat glass, with liftable curtains and actuators for lifting the curtains, a method to automatically lift the curtains of the exit hood of the machine comprising:

a) directing an incident light beam from a light emitter placed over an edge of the glass ribbon, on a surface of the glass ribbon to be reflected thereby as a reflected light beam;

b) receiving the reflected light beam with a light beam receiver;

c) deriving a signal from the receiver representative of an absence of the reflected light beam because of a break in the glass ribbon;

d) feeding the signal representative of an absence of the reflected light beam to a controller;

e) deriving a plurality of operating control signals in the controller in response to the signal representative of an absence of the reflected light beam; and f) providing a first operating control signal of said plurality of operating control signals to the actuators for lifting the curtains.

5. The method of claim 4, wherein the float glass manufacturing machine also includes a reheating system, glass edge follower mechanism and an emergency alarm, and further comprising providing a second operating control signal of said plurality of operating control signals to the reheating system to operate said system to maintain thermal equilibrium in said machine, providing a third operating control signal of said plurality of operating control signals to the glass edge follower mechanism to retract it from the glass ribbon to prevent the glass from being clogged therein, and providing a fourth operating control signal of said plurality of operating control signals to said emergency alarm to trigger it.

* * * * *